United States Patent [19]

Israel

[11] Patent Number: 5,782,894
[45] Date of Patent: Jul. 21, 1998

[54] DEVICE AND METHOD FOR IMPROVING OCULAR FOCUSING AT NEAR VISION POINTS

[76] Inventor: Ben Israel, 3061 Market Ave., Suite 2, Fayetteville, Ark. 72703

[21] Appl. No.: 810,892

[22] Filed: Mar. 5, 1997

[51] Int. Cl.⁶ ................................................. A61N 1/08
[52] U.S. Cl. ........................................................ 607/53
[58] Field of Search .................................... 607/53, 54

[56] References Cited

U.S. PATENT DOCUMENTS

| | | |
|---|---|---|
| 4,271,841 | 6/1981 | Friedman . |
| 4,603,697 | 8/1986 | Kamerling . |
| 4,989,605 | 2/1991 | Rossen . |
| 5,109,846 | 5/1992 | Thomas . |
| 5,360,438 | 11/1994 | Fisher . |
| 5,489,299 | 2/1996 | Schachar . |
| 5,496,355 | 3/1996 | Lipsky . |

*Primary Examiner*—Scott M. Getzow
*Attorney, Agent, or Firm*—Boyd D. Cox

[57] ABSTRACT

A device and method for treating presbyopia by which the ciliary muscles of the eyes are electrically stimulated when the internal rectus muscles of the eyes are activated in order to focus the eyes on objects within the near field of vision. The amounts of electrical stimulation can be adjusted according to the individual needs of a patient and are preferably in direct proportion to the amounts of contraction of the internal muscles.

31 Claims, 5 Drawing Sheets

DEVICE AND METHOD FOR IMPROVING OCULAR FOCUSING AT NEAR VISION POINTS

BACKGROUND OF THE INVENTION

The present invention is directed to a device and method for effectively treating presbyopia by restoring a patient's ability to focus clearly on objects in the patient's near field of vision. It is the first cure for presbyopia which is controlled by a natural convergence of the eyes occurring when the eyes fixate on a close object and which does not require the adaptation of external lenses.

Presbyopia is the loss of near point vision which is marked by a decrease in the amplitude of accommodation resulting in the inability of the lens to focus on a near point. It is caused primarily by a loss of muscle tone in the ciliary muscle of the eye, coupled with an increased rigidity of the lens. A person having presbyopia is unable to focus his/her eyes on objects in his/her near field of vision and, therefore, fails to see the objects clearly.

Presbyopia is believed to occur as a result of aging and progressively worsens as a person gets older. Most people over the age of 45 suffer from this type of vision failure. After the onset of presbyopia, reading or doing any type of close work becomes difficult, if not impossible.

Eyeglasses, such as reading glasses and bifocals, are the most common means for treating presbyopia, but have several drawbacks. Eyeglasses are external lenses which supplement the refractive power of the crystalline lens to bring an object into focus. The lenses of eyeglasses adjust a person's vision only for the specific distance to which the lenses are prescribed. Consequently, a pair of eyeglasses prescribed to focus a patient's eyes at a given distance will not sharply focus the patient's eyes on an object in the patient's near field of vision when the object is located nearer or farther from the viewer than such given distance. Therefore, the patient's ability to effectively focus within the near vision field remains limited even when wearing eyeglasses.

Wearing eyeglasses is also a nuisance; they can be uncomfortable and easily lost or broken. Moreover, they are of no benefit when a patient is unable to wear them or chooses not to do so.

Reading glasses adjust the eyes to perform near vision tasks, but generally are not worn when the user chooses to focus upon a distant object. Consequently, reading glasses are frequently put on and taken off to alternate between near focusing tasks and distant focusing tasks. It is a further inconvenience to have to carry such glasses around in the event they might be needed.

Even with bifocal lenses, which enable a person to perform near focusing and distant focusing tasks using one pair of eyeglasses, the person is still hampered at a near vision task because of the uncomfortable and awkward positions the head must be held in order to see through the areas of the lenses designed for near vision.

For the foregoing reasons, there is a need for a device and method which conveniently treat the inability to see near objects clearly, which effectively focus the eyes at all specific near vision points, and which eliminate any requirement of eyeglasses to correct for presbyopia.

SUMMARY OF THE INVENTION

The present invention is directed to a device and method that satisfies the need of restoring the loss of near vision resulting from presbyopia without the use of eyeglasses. A device and method are provided which focus the eyes upon a near object by electrically stimulating the ciliary muscles when the eyes converge to view the near object. Preferably, the ciliary muscles are stimulated by an amount that is in direct proportion to the contraction of the internal rectus muscles to ensure that the eyes focus to the specific distance of the near object.

In a preferred embodiment of the invention, a sensor is surgically installed on the internal rectus muscle of each eye; a stimulator is surgically installed on the ciliary muscle of each eye; and a control unit which communicates between the sensors and stimulators is surgically installed under the skin.

When the internal rectus muscles are activated by the eyes fixating on an object in the near field of vision, the sensors detect the contraction and generate activation signals that are transmitted to the control unit. The control unit processes the activation signals and generates stimulation signals. The stimulation signals are developed into electrical stimulations which are transmitted to the stimulators and applied to the ciliary muscles. The ciliary muscles contract in response to the electrical stimulations which effect focusing of the eyes on the near object. At such time that the internal rectus muscles cease 5 contracting, the activation signals stop and the focusing process stops, whereupon the eyes return to a distant vision posture.

It is known that the loss of near vision due to presbyopia increases as a person ages. Other factors can also affect a person's near vision. Therefore, it is preferred that the amounts of electrical stimulation applied to the ciliary muscles to effect near focusing be adjustable. This can be accomplished by the inclusion of regulators, such as variable resistors, in the control unit. The regulators can be selectively set so as to establish the amounts of electrical stimulation applied to the ciliary muscles and thereby compensate for changes in a person's near vision capability.

Overall, the amount of electrical stimulation directed to the stimulator and applied to the ciliary muscle is of a frequency to provide sufficient contraction of the ciliary muscle to focus the eye at any specific point in the near field of vision to which the eye is directed.

It is an object of the present invention to provide an improved method and apparatus for treating presbyopia by electrically stimulating the ciliary muscles in response to activation of the internal rectus muscles.

It is a further object of the present invention to provide a device and method which corrects eyesight for reading and performing other near vision tasks without the use of eyeglasses.

It is a further object of the present invention to provide a device and method that enables the eyes to focus at all specific distances within the near field of vision.

It is a further object of the present invention to provide a device and method for focusing the eyes at a near point wherein the focusing activity is automatically stimulated by the natural convergence of the eyes to view a close object.

It is a further object of the present invention to provide a device and method for focusing the eyes upon a near object wherein the focusing activity is automatically stimulated by the eyes fixating on such object.

It is a further object of the present invention to provide a device and method for electrically stimulating the ciliary muscles to assume a more aggressive posture for overcoming the loss of ciliary muscle tone and increased rigidity of the crystalline lenses and ultimately focus the eyes on a nearby point.

It is a further object of the present invention to provide a device and method for correcting presbyopia by electrically stimulating the ciliary muscles wherein the amounts of electrical stimulation can be adjusted for changing conditions, such as the aging of the patient.

BRIEF DESCRIPTION OF THE DRAWINGS

Reference is made to the accompanying drawings in which are shown illustrative embodiments of the invention and from which novel features and advantages will be apparent.

DETAILED DESCRIPTION

Figure 1:
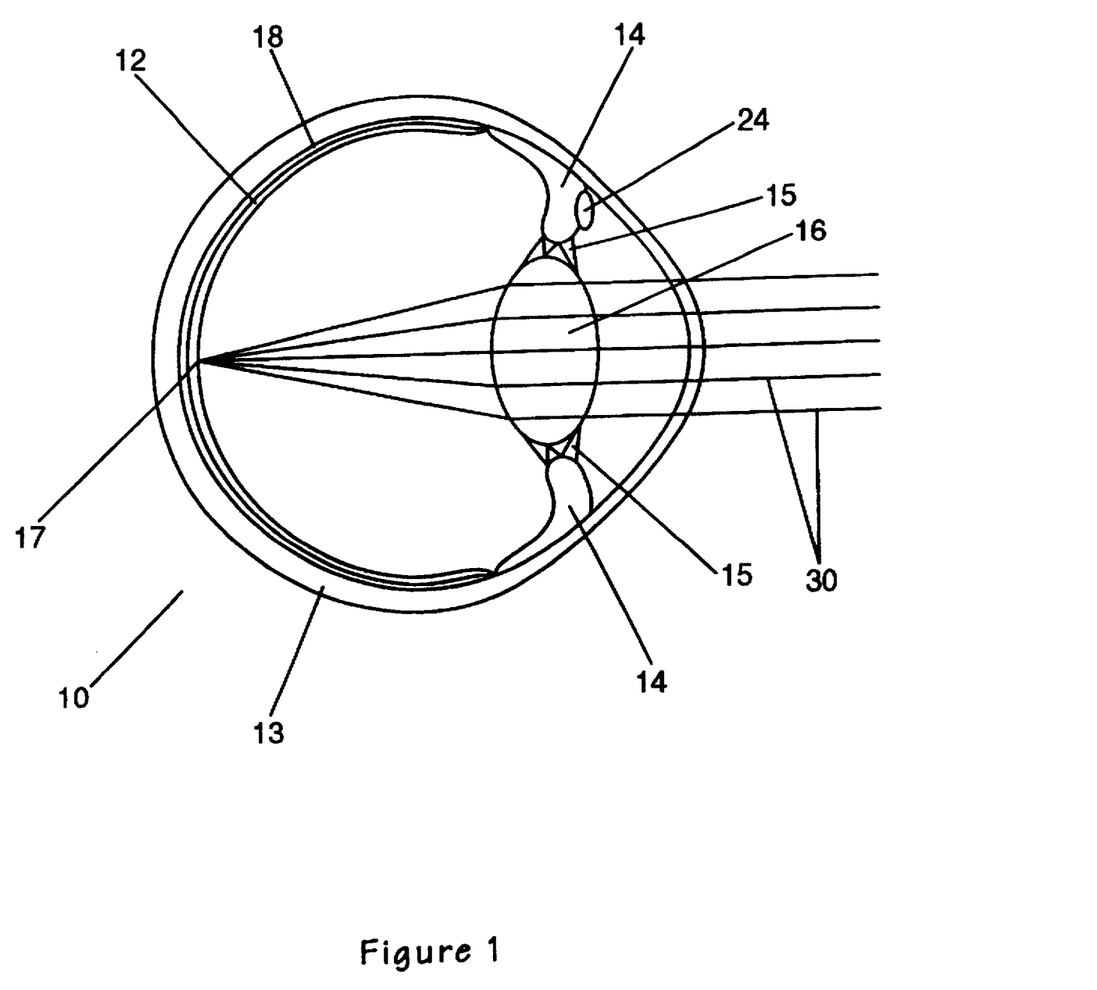
FIG. 1 is a diagram depicting a cross-sectional view of an eye having a device embodying features of the present invention installed therein, and wherein the eye is focused on a near object by such device.
Figure 2:
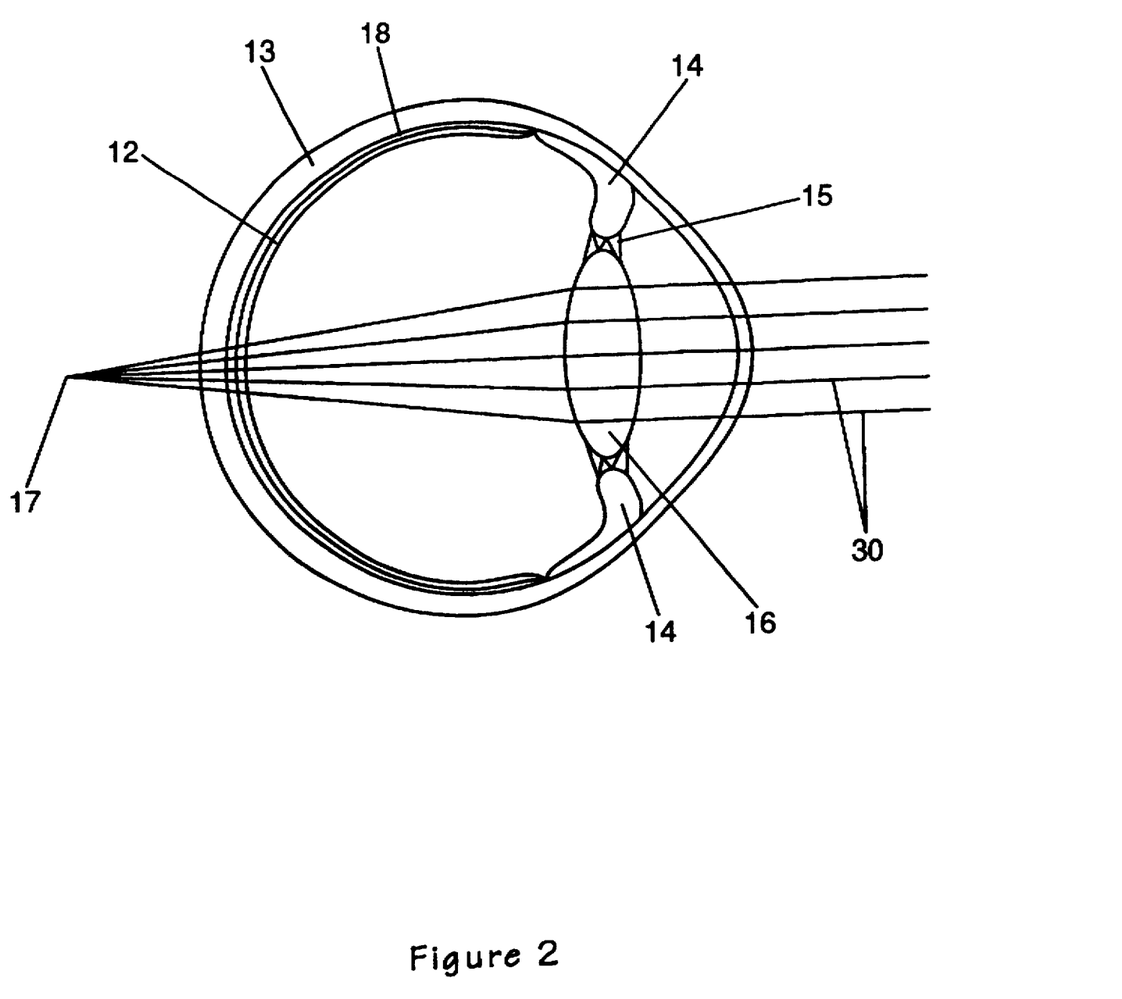
FIG. 2 is a diagram depicting a cross-sectional view of a presbyotic eye unable to focus on a near object.
Figure 3:
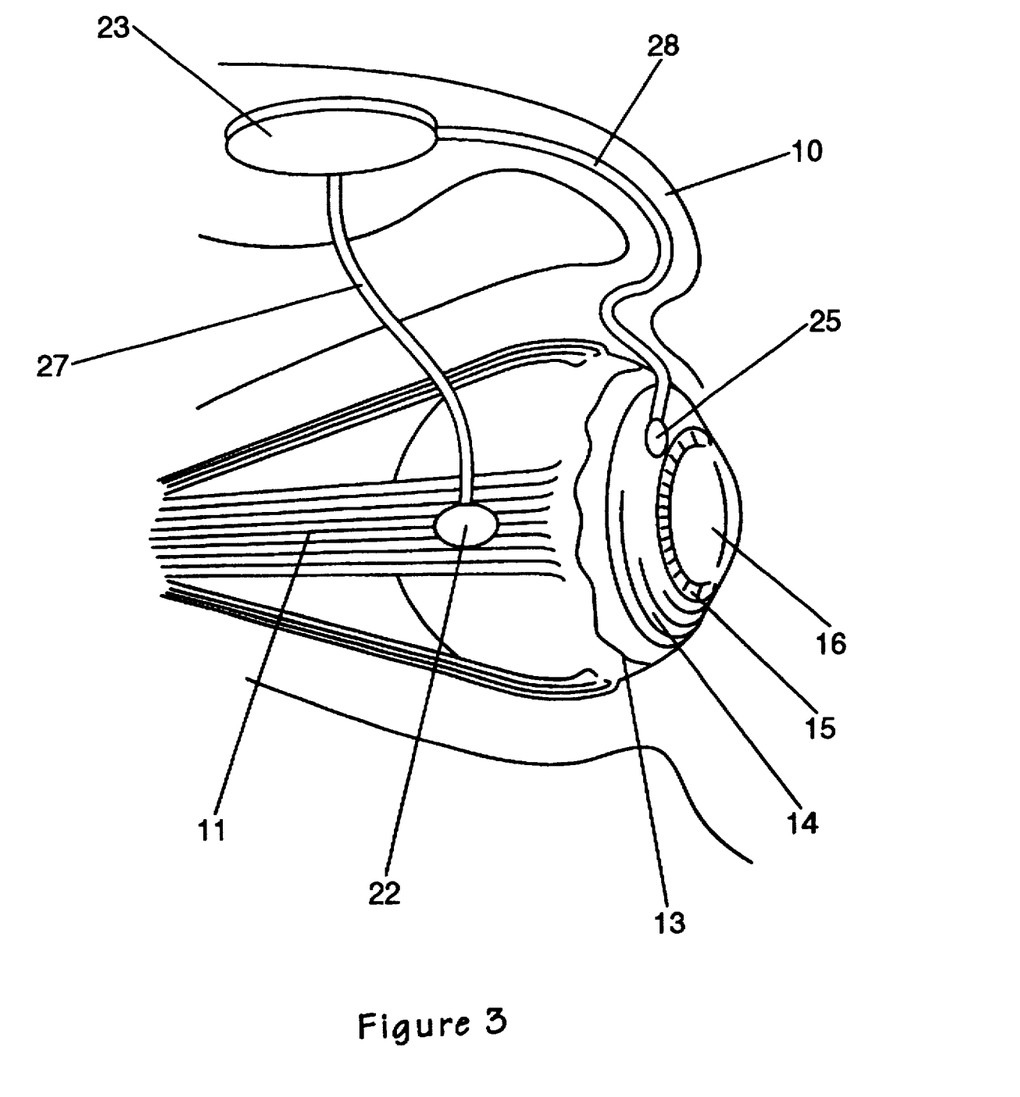
FIG. 3 is a schematic cut-away side view depicting an eye with an embodiment of the invention installed therein.

Referring to FIGS. 1 and 2, the eye (10) includes a crystalline lens (16) suspended within the eyeball. Zonular fibers (15), attached to the perimeter of the lens, extend radially outwardly therefrom and attach to the ciliary muscle (14). The ciliary muscle (14) is embedded in an anterior portion of the choroid (18). The choroid (18) is a layer of the eye extending between the inner surface of the eye's outer covering or schlera (13) and the retina (12).

Figure 4:
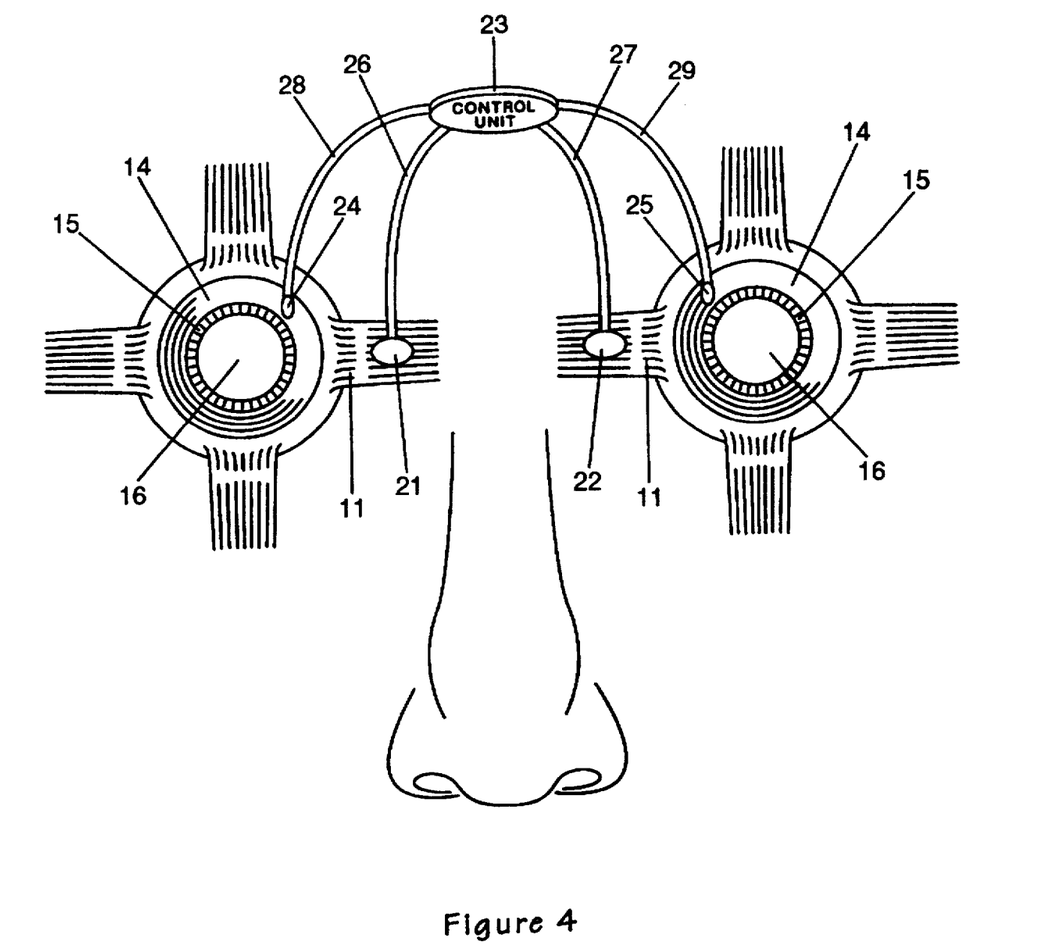
FIG. 4 is a schematic frontal view of an embodiment of the present invention installed in a patient's eyes.

Inward movement of the eyes, i.e. eye convergence, is controlled by a pair of ocular muscles known as the internal rectus muscles. First and second internal rectus muscles (11) are disposed on the internal sides of first and second eyes, respectively, as shown in FIG. 4.

In order for a person to see an object in focus, the light rays (30) reflected by the object must be focused at a point (17) on the surface of the eye's retina (12) as shown in FIG. 1. The position of this focal point (17) is adjusted by changing the shape of the crystalline lens (16) by increasing or decreasing the convexity of the lens.

Focusing of the eyes can be directly tied to the positioning of the eyes. When an object is viewed at a point in a person's near field of vision, the eyes naturally converge or fixate on that object. The near field of vision is defined herein to include distances less than approximately 20 feet from the viewer. The internal rectus muscles interact with the ciliary muscles in such a way that when the former simultaneously contract, the latter also contract. This stimulates the eyes to attempt to focus upon the object in the near field of vision.

In a non-presbyotic eye, near focusing occurs when the internal rectus muscles simultaneously contract and the eyes converge on an object in the near field of vision. The ciliary muscle contracts, moving inwardly toward the respective lens and loosening the zonular fibers, thereby releasing the outward pulling force exerted by the fibers on the perimeter of the crystalline lens. Due to its natural elasticity, the lens is allowed to change shape by widening in the anterior-posterior direction, which increases the lens' convexity. This leads to an increase in the lens' refractive power whereby the lens effects focusing of the eye on the near object.

FIG. 2 shows how the lens (16) of a presbyotic eye fails to bring a near object into focus. Light (30) reflected from a near object enters the eye as shown. The lens (16) is flattened and unable to bend or refract the light (30) enough to adjust the focal point (17) to rest on the retina (12) of the eye. As a result, the near object is not in focus and appears unclear to the viewer.

The amount of eye convergence is a function of the distance that a near object is from the viewer and determines how much the crystalline lenses must adjust or change shape to bring the near object into focus. For example, within a near field of vision, the closer an object is moved toward the viewer, the more the eyes of the viewer must converge to fixate on the object. As a result, the more the internal rectus muscles must contract to move the eyes inwardly and the more convex the eyes' lenses must become in order to focus the viewer's eyes on the object.

Figure 5:
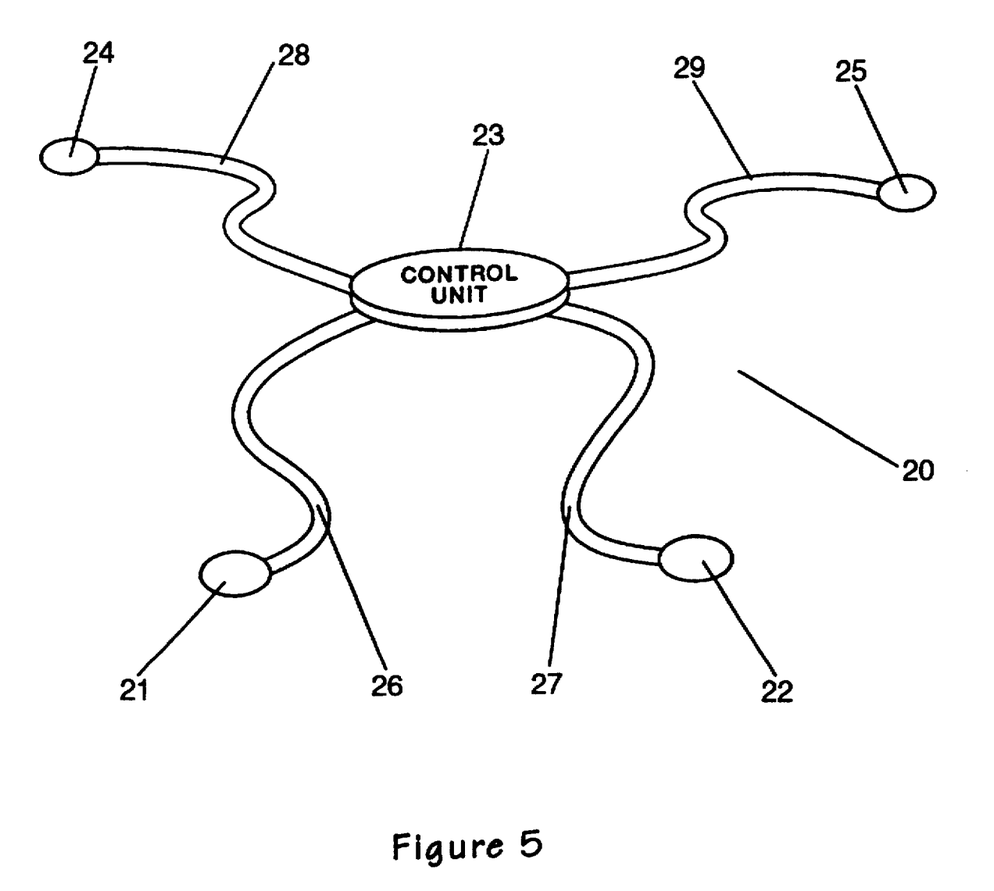
FIG. 5 is a diagram of a version of a device embodying features of the present invention.

Referring to FIG. 5, the device (20), embodying features of the present invention, is shown to include first (21) and second (22) sensors, first (24) and second (25) stimulators and a control unit (23).

Each of the first (21) and second (22) sensors communicates with the control unit (23) via a respective first (26) and second (27) wire. The first wire (26) extends between the first sensor (21) and the control unit (23), while the second wire (27) extends between the second sensor (22) and the control unit (23). Each of the first (21) and second (22) sensors is an electrode.

The control unit (23) is a single integrated circuit such as disclosed by Lipsky's U.S. Pat. No. 5,496,355, which is incorporated herein by reference. The control unit (23) includes a logic circuit and a pulse generator complex which further includes first and second variable resistors. The variable resistors in the embodiment of the present device are similar to Lipsky's variable resistor in that they act to fine tune or regulate the signal impulses, but in the present device, the variable resistors, which are selectively adjustable, are designed to regulate the amounts of the electrical stimulations that are delivered to the ciliary muscles. It is known that a muscle responds to an increase in the frequency of an electrical impulse by an exponential increase in contraction of the muscle. It is appreciated herein that an increased amount of electrical stimulation refers to an increase in the frequency of impulses of the electrical stimulation.

The third (28) and fourth (29) wires are each attached at one end to the control unit (23). The other end of the third wire (28) is attached to the first stimulator (24) and the other end of the fourth wire (29) is attached to the second stimulator (25). Each of the first and second stimulators (24,25) is an electrode.

Referring to FIG. 4, the first and second sensors (21,22) are shown to be surgically implanted, respectively, in first and second eyes of a patient. The first sensor (21) is installed on a first internal rectus muscle (11) of the first eye and the second sensor (22) is installed on a second internal rectus muscle (11) of the second eye.

The first stimulator (24) is surgically installed on a first ciliary muscle (14) of the first eye. The second stimulator (25) is surgically installed on a second ciliary muscle (14) of the second eye.

The control unit (23) is surgically implanted under the skin in a concealed location such as behind the ear or above the collar bone. First (26) and second (27) wires are subcutaneously installed extending from each respective sensor (21,22) to the control unit (23). The third (28) and fourth (29) wires are implanted under the skin and extend from the control unit (23) to a respective stimulator (24,25).

A preferred method of use embodying features of the present invention includes the device (20) surgically implanted in a patient having presbyopia. When the patient views certain objects in the patient's near field of vision, the patient's eyes converge to fixate on such objects. Both the first and second internal rectus muscles are activated and contract to direct the eyes inwardly.

The first sensor (21) detects the activation of the first internal rectus muscle (11) and the amount of the muscle's contraction. Likewise, the activity of the second internal rectus muscle (11) is detected by the second sensor (22) and the amount that the muscle contracts is determined thereby. The sensors (21,22) detect the activity of the internal rectus muscles (11) by sensing the neuronal impulses sent to the muscles.

In response to the contraction activity of the internal rectus muscles, the first sensor (21) generates a first activation signal indicating that activation of the first internal rectus muscle is occurring and the amount of contraction that is occurring and the second sensor generates a second activation signal indicating that activation of the second internal rectus muscle is occurring and the amount of contraction that is occurring.

The first and second activation signals are transmitted to the control unit (23) by the first (26) and second (27) wires, respectively. Within the control unit (23), the logic circuit processes the first and second activation signals and determines that the eyes of the patient are converging to view the object. The logic circuit then generates a first stimulation signal and a second stimulation signal. When the eyes are not converging, the logic circuit does not generate the stimulation signals.

The stimulation signals generated by the logic circuit are sent to the pulse generator complex which is contained within the control unit. The pulse generator complex develops the first stimulation signal into a first electrical stimulation and develops the second stimulation signal into a second electrical stimulation. First and second variable resistors regulate the amounts of respective first and second electrical stimulations.

The electrical stimulations developed by the pulse generator complex and regulated by the variable resistors preferably are of amounts that are directly proportional to the amounts of contraction of the respective internal rectus muscles to ensure that each eye focuses to the specific distance of the near object. Therefore, the first electrical stimulation is directly proportional to the amount of contraction of the first internal rectus muscle and the second electrical stimulation is directly proportional to the amount of contraction of the second internal rectus muscle.

The first electrical stimulation is then transmitted from the control unit (23) to the first stimulator (24) via the third wire (28). Likewise, the second electrical stimulation is sent from the control unit (23) to the second stimulator (25) via the fourth wire (29).

The first stimulator (24) applies the first electrical stimulation to the first ciliary muscle (14) and the second stimulator (25) applies the second electrical stimulation to the second ciliary muscle (14) of the patient's eyes.

For each eye, the ciliary muscle contracts in response to the electrical stimulation and moves radially inwardly towards the perimeter of the lens (16). The resultant inward movement of the ciliary muscle (14) loosens the attached zonular fibers (15) and relaxes the outward tensile force on the lens (16) exerted by the zonular fibers. This allows the lens to widen in the anterior-posterior direction, thereby increasing the convexity and refractive power of the lens to bring the eye into focus on the near object.

When the object is removed from the patient's near field of vision, the eyes are no longer directed inwardly, and the internal rectus muscles (11) are relaxed. The sensors (21,22) no longer detect any activation of the internal rectus muscles, and therefore stop generating activation signals. Cessation of the activation signals stops generation and transmission of the electrical stimulations being delivered to the ciliary muscles and the ciliary muscles relax. Relaxation of the ciliary muscles tightens the zonular fibers around the lenses and the lenses are pulled back into tension. This tension flattens the lenses, thereby decreasing their convexity and the eyes assume a distant vision posture.

In a preferred embodiment of the present invention, the variable resistors can be adjusted to regulate the amount of the electrical stimulations delivered to the ciliary muscle, both before and after installation of the device in a patient.

The amount of the electrical stimulations applied to the ciliary muscles that is required to focus the eyes varies from person to person. To compensate for these variations, the variable resistors can be adjusted at the time of installation to regulate and thereby effect any selective changes to the overall amounts of the electrical stimulations which are developed by the pulse generator complex and that are required for the focusing needs of an individual patient.

After the device has been installed in a patient, it may be necessary to make adjustments to the variable resistors when the patient's near focusing capabilities change. Since presbyopia typically worsens with age, there is a likelihood that the overall amount of electrical stimulation applied to the ciliary muscle will need to be increased periodically to maintain the proper amount of ciliary muscle contraction for focusing the patient's eyes in the near field of vision. The variable resistors can be adjusted upon removal or in situ by methods known to those skilled in the art. In such manner, the amount of electrical stimulations needed for focusing the patient's eyes on a near object can be properly maintained.

The previously described versions of the present invention have many advantages, including the elimination of the need for eyeglasses to treat presbyopia.

Preferred embodiments of the present invention improve ciliary muscle tone and stimulate the ciliary muscle to a more aggressive posture. This enhances the strength of the ciliary muscle to overcome the tendency of the crystalline lens to become rigid, thereby enabling the presbyotic eye to focus on near objects.

As stated earlier, as a person ages, the person's ability to focus on nearby points diminishes. The amount of electrical stimulation needed to adequately stimulate the ciliary muscle of a person aged 45 to achieve near focusing would normally be less than the amount required when that same person reaches 50 years of age. In a preferred embodiment of the present invention, the electrical stimulation can be adjusted to compensate for any deterioration in the eye's ability to focus on nearby objects.

The devices and methods of preferred embodiments of the present invention act to restore a person's ability to focus on objects at all specific distances within the person's near field of vision. This ability is not attainable with eyeglasses.

Since preferred embodiments of the invention are activated by the eyes converging to view an object, the near focusing of the eyes is automatically controlled. The user does not have to perform any manual tasks to focus the eyes. The eyes only have to converge on an object in the near field of vision and the eyes are automatically brought into focus on such object.

Although the present invention has been described in considerable detail with reference to certain preferred versions thereof, other versions are possible. Therefore, the spirit and scope of the appended claims should not be limited to the description of the preferred versions contained herein.

What is claimed:

1. An ocular focusing device for a patient having a first eye with a first internal rectus muscle and a first ciliary muscle and a second eye with a second internal rectus muscle and a second ciliary muscle, the device comprising:
   a first sensor adapted to be installed on the first internal rectus muscle of the patient's first eye to detect activation of the first internal rectus muscle;
   a second sensor adapted to be installed on the second internal rectus muscle of the patient's second eye to detect activation of the second internal rectus muscle;
   at least one stimulator adapted to be installed on at least one ciliary muscle of the patient's eyes to stimulate said at least one ciliary muscle to contract when the internal rectus muscles are activated.

2. The ocular focusing device of claim 1, further comprising a controller to adjust the amount of stimulation applied by the least one stimulator to the at least one ciliary muscle.

3. The ocular focusing device of claim 1, further comprising a control unit communicating between the sensors and the at least one stimulator.

4. The ocular focusing device of claim 3, wherein the first sensor generates a first activation signal indicating that the first internal rectus muscle has been activated and the second sensor generates a second activation signal indicating that the second internal rectus muscle has been activated.

5. The ocular focusing device of claim 4, wherein the control unit is an integrated circuit which further comprises:
   a logic circuit for receiving and processing the activation signals and generating at least one stimulation signal; and
   a pulse generator complex for developing the at least one stimulation signal into an at least one electrical stimulation which is transmitted to the at least one stimulator.

6. The ocular focusing device of claim 5, wherein the pulse generator complex further comprises at least one variable resistor for regulating the amount of the at least one electrical stimulation which is transmitted to the at least one stimulator.

7. The ocular focusing device of claim 5, wherein the at least one stimulator comprises:
   a first stimulator adapted to be installed on the first ciliary muscle, and
   a second stimulator adapted to be installed on the second ciliary muscle; and the at least one stimulation signal comprises:
   a first stimulation signal developed from the first activation signal, and a second stimulation signal developed from the second activation signal; and the at least one electrical stimulation comprises:
   a first electrical stimulation developed from the first stimulation signal and transmitted to the first stimulator, and
   a second electrical stimulation developed from the second stimulation signal and transmitted to the second stimulator.

8. The ocular focusing device of claim 7, wherein the first and second stimulators each comprise an electrode, and the first and second sensors each comprise an electrode.

9. The ocular focusing device of claim 7, wherein the first activation signal further indicates the amount of contraction of said first internal rectus muscle and the second activation signal further indicates the amount of contraction of said second internal rectus muscle.

10. The ocular focusing device of claim 9, wherein the first electrical stimulation is in an amount that is directly proportional to the amount of contraction of the first internal rectus muscle and the second electrical stimulation is in an amount that is directly proportional to the amount of contraction of the second internal rectus muscle.

11. An ocular focusing device for a patient having a first eye with a first ciliary muscle and a second eye with a second ciliary muscle, the device comprising:
   at least one sensor for sensing convergence of the patient's eyes; and
   at least one stimulator adapted to be installed on at least one ciliary muscle of the patient's eyes to stimulate said at least one ciliary muscle to contract when the eyes are converging.

12. An ocular focusing device for a patient having a first eye with a first ciliary muscle and a second eye with a second ciliary muscle, the device comprising:
   at least one sensor for sensing when the eyes are fixating on a point in the patient's near field of vision; and
   at least one stimulator adapted to be installed on at least one ciliary muscle of the patient's eyes to stimulate said at least one ciliary muscle to contract when the eyes are fixating on said point.

13. An ocular focusing device for a patient having a first eye with a first internal rectus muscle and a first ciliary muscle and a second eye with a second internal rectus muscle and a second ciliary muscle, the device comprising:
   a means for sensing activation of the internal rectus muscles of the patient; and
   a means for stimulating at least one ciliary muscle of the patient when the internal rectus muscles are activated.

14. The ocular focusing device of claim 13, further comprising a means for controlling the amount of stimulation applied by the means for stimulating to the at least one ciliary muscle.

15. The ocular focusing device of claim 13, further comprising a control means communicating between the means for sensing and the means for stimulating.

16. The ocular focusing device of claim 15, wherein the means for sensing generates at least one activation signal indicating that the internal rectus muscles have been activated.

17. The ocular focusing device of claim 16, wherein the control means comprises a control unit being an integrated circuit and having:
   a logic circuit for receiving and processing the at least one activation signal and generating at least one stimulation signal; and
   a pulse generator complex for developing the at least one stimulation signal into at least one electrical stimulation which is transmitted to the means for stimulating.

18. The ocular focusing device of claim 17, wherein the pulse generator complex further comprises means for regulating the amount of the at least one electrical stimulation which is transmitted to the means for stimulating.

19. The ocular focusing device of claim 17, wherein the means for stimulating comprises:
   a first means for stimulating the first ciliary muscle, and
   a second means for stimulating the second ciliary muscle; and the at least one electrical stimulation comprises:

a first electrical stimulation developed from the at least one stimulation signal and transmitted to the first means for stimulating, and a second electrical stimulation developed from the at least one stimulation signal and transmitted to the second means for stimulating.

20. The ocular focusing device of claim 19, wherein the means for sensing comprises at least one electrode.

21. The ocular focusing device of claim 19, wherein each of the first and second means for stimulating comprises at least one electrode.

22. The ocular focusing device of claim 17, wherein the at least one activation signal further indicates the amount of contraction of the internal rectus muscles.

23. The ocular focusing device of claim 22, wherein the at least one electrical stimulation is in an amount that is directly proportional to the amount of contraction of the internal rectus muscles.

24. An ocular focusing device for a patient having a first eye with a first internal rectus muscle and a first ciliary muscle and a second eye with a second internal rectus muscle and a second ciliary muscle, the device comprising:

a means for sensing convergence of the patient's eyes; and a means for stimulating at least one ciliary muscle of the patient when the eyes are converging.

25. An ocular focusing device for a patient having a first eye with a first ciliary muscle and a second eye with a second ciliary muscle, the device comprising:

a means for sensing when the eyes are fixating on a point in the patient's near field of vision; and a means for stimulating at least one ciliary muscle of the patient when the eyes are fixating on said point.

26. An ocular focusing device for treating presbyopia in a patient having a first eye with a first internal rectus muscle and a first ciliary muscle and a second eye with a second internal rectus muscle and a second ciliary muscle, wherein each eye further includes zonular fibers and a crystalline lens, said device comprising:

a first sensor comprising an electrode adapted to be disposed on the first internal rectus muscle for sensing activation and determining an amount of contraction of said first internal rectus muscle, wherein the first sensor generates a first activation signal indicating activation and the amount of contraction of said first internal rectus muscle;

a second sensor comprising an electrode adapted to be disposed on said second internal rectus muscle for sensing activation and determining an amount of contraction of said second internal rectus muscle, wherein said second sensor generates a second activation signal indicating activation and the amount of contraction of said second internal rectus muscle;

a control unit comprising:

a logic circuit for processing the first and second activation signals and generating first and second stimulation signals, respectively; and a pulse generator complex for developing the first and second stimulation signals into first and second electrical stimulations, respectively, wherein said pulse generator complex further comprises first and second variable resistors for adjusting the amount of said first and second electrical stimulations, respectively, wherein said first electrical stimulation is an amount that is directly proportional to the amount of contraction of the first internal rectus muscle and the second electrical stimulation is an amount that is directly proportional to the amount of contraction of the second internal rectus muscle;

a first stimulator comprising an electrode adapted to be disposed on the first ciliary muscle for applying the first electrical stimulation to said first ciliary muscle, wherein said first electrical stimulation causes said first ciliary muscle to contract;

a second stimulator comprising an electrode adapted to be disposed on the second ciliary muscle for applying the second electrical stimulation to said second ciliary muscle, wherein said second electrical stimulation causes said second ciliary muscle to contract;

a first and second wire extending to the control unit from the first and second sensors, respectively, wherein the first wire transmits the first activation signal from the first sensor to the control unit and the second wire transmits the second activation signal from the second sensor to the control unit;

a third and fourth wire extending from the control unit to the first and second stimulators, respectively, wherein the third wire transmits the first electrical stimulation from the control unit to the first stimulator and the fourth wire transmits the second electrical stimulation from the control unit to the second stimulator;

wherein the presence of an object in the patient's near field of vision stimulates activation of the first and second internal rectus muscles to direct the eyes to said object; the first and second sensors detecting the activation of the first and second internal rectus muscles of the first and second eyes, respectively, determining the amounts of contraction of the first and second internal rectus muscles, respectively, and generating the first and second activation signals indicating activation and the amount of contraction of the first and second internal rectus muscles, respectively; the first and second wires transmitting the first and second activation signals from the first and second sensors, respectively, to the control unit where the logic circuit processes the first and second activation signals and generates the first stimulation signal from the first activation signal and generates the second stimulation signal from the second activation signal; the first and second stimulation signals being sent to the pulse generator complex and being developed into the first and second electrical stimulations, respectively; the amounts of the respective first and second electrical stimulations being adjusted by the variable resistors; wherein the first and second electrical stimulations are in amounts that are directly proportional to the amounts of contraction of the first and second internal rectus muscles, respectively; the first and second electrical stimulations being transmitted by the third and fourth wires to the first and second stimulators, respectively, and being applied to the first and second ciliary muscles, respectively; the first and second ciliary muscles contracting in response to the respective first and second electrical stimulations, causing the zonular fibers of the respective first and second eyes to loosen, allowing the crystalline lenses of the respective first and second eyes to become more convex, thereby focusing the eyes on the object in the near field of vision; and upon relaxation of the first and second internal rectus muscles, the first and second sensors cease transmission of the first and second activation signals to the control unit causing the first and second electrical stimulations to the respective first and second ciliary muscles to stop, whereupon the eyes assume a distant vision posture.

27. A method for focusing the eyes of a patient in a near field of vision wherein the patient has a first eye with a first internal rectus muscle and a first ciliary muscle and a second eye with a second internal rectus muscle and a second ciliary muscle, the method comprising the steps of:

sensing activation of the first and second internal rectus muscles of the patient; and stimulating at least one of the first and second ciliary muscles of the patient when both of the internal rectus muscles are activated.

28. The method for focusing the eyes of a patient of claim 27, further comprising stimulating at least one of the first and second ciliary muscles in an amount directly proportional to the amount of activation of the first and second internal rectus muscles of the patient.

29. A method for focusing the eyes of a patient in a near field of vision wherein the patient has a first eye with a first ciliary muscle and a second eye with a second ciliary muscle, the method comprising the steps of:

sensing convergence of the patient's eyes; and stimulating at least one of the first and second ciliary muscles of the patient when the eyes converge.

30. A method for focusing the eyes of a patient in a near field of vision, wherein the patient has a first eye with a first ciliary muscle and a second eye with a second ciliary muscle, the method comprising the steps of:

sensing when at least one of the eyes is fixated on a point located in the patient's near field of vision; and stimulating at least one of the first and second ciliary muscles of the patient when the eyes are fixated on said point.

31. A method for focusing a patient's eyes on a point in a near field of vision wherein the patient has a first eye with a first internal rectus muscle and a first ciliary muscle and a second eye with a second internal rectus muscle and a second ciliary muscle, comprising the steps of:

sensing the activation of the internal rectus muscles of the first and second eyes;

determining the amounts of contraction of the internal rectus muscles;

generating activation signals to indicate that contraction of the internal rectus muscles is occurring and the amounts of contraction;

transmitting the activation signals to a control unit;

processing the activation signals;

generating stimulation signals from the activation signals;

developing the stimulation signals into electrical stimulations;

regulating the electrical stimulations, wherein the amount of the electrical stimulations is directly proportional to the amount of contraction of the internal rectus muscles;

transmitting the electrical stimulations to stimulators in the ciliary muscles;

stimulating the ciliary muscles to contract in response to the electrical stimulations to focus the eyes on the point in the near field of vision.

* * * * *